(12) United States Patent
Baur et al.

(10) Patent No.: US 6,949,381 B2
(45) Date of Patent: Sep. 27, 2005

(54) IMMORTALIZED HUMAN SKIN CELL LINES AND NOVEL SERUM-FREE MEDIUM USEFUL FOR THE PRODUCTION THEREOF

(75) Inventors: Markus Baur, Lausanne (CH); Catherine Mace, Lutry (CH); Armand Malnoe, Dommartin (CH); Andrea M. A. Pfeifer, St-Légier (CH); Marcelle Regnier, Paris (FR)

(73) Assignee: Nestec S.A., Vevey (CH)

( * ) Notice: Subject to any disclaimer, the term of this patent is extended or adjusted under 35 U.S.C. 154(b) by 320 days.

(21) Appl. No.: 09/982,649

(22) Filed: Oct. 18, 2001

(65) Prior Publication Data

US 2002/0042129 A1 Apr. 11, 2002

Related U.S. Application Data

(63) Continuation of application No. 09/091,483, filed as application No. PCT/EP96/05812 on Dec. 19, 1996, now Pat. No. 6,423,540, which is a continuation of application No. 08/576,483, filed on Dec. 21, 1995, now abandoned.

(51) Int. Cl.$^7$ .................................................. C12N 5/00
(52) U.S. Cl. ...................... 435/371; 435/325; 435/366; 435/467
(58) Field of Search ................................. 435/371, 325, 435/366, 467

(56) References Cited

U.S. PATENT DOCUMENTS

| | | | |
|---|---|---|---|
| 4,940,666 A | 7/1990 | Boyce et al. | |
| 5,292,655 A | 3/1994 | Wille, Jr. | |
| 6,423,540 B2 * | 7/2002 | Baur et al. | |

FOREIGN PATENT DOCUMENTS

| DE | 196 17 261 | 11/1996 |
|---|---|---|
| WO | WO 95/27510 | 10/1995 |

OTHER PUBLICATIONS

P. Boukamp et al., "Normal Keratinization in a Spontaneously Immortalized Aneuploid Human Keratinocyte Cell Line", *The Journal of Cell Biology*, 106:761–771 (1988).

A. Pfeifer et al., "Highly efficient establishment of immortalized cells from adult human liver", *Methods on Cell Science*, 17:83–89 (1995).

M. Pittelkow et al., "New Techniques for the In Vitro Culture of Human Skin Keratinocytes and Perspectives on Their Use for Grafting of Patients With Extensive Burns", *Mayo Clin Proc*, 61:771–777 (1986).

H. Navsaria et al., "Culturing skin in vitro for wound therapy", *TIBTECH* 13:91–100 (1995).

E. Sbano et al., "Pemphigus Antibodies Fixation and Keratinocyte Differentiation in Organ Cultures", *Arch Dermatol Res*, 273:9–14 (1982).

V. Steinkraus et al., "High density of beta$_2$–adrenoceptors in a human keratinocyte cell line with complete epidermal differentiation capacity (HaCaT)", *Arch Dermatol Res*, 283:328–332 (1991).

Derwent WPI Acc No: 97–022262/199703, English language abstract of Germany 196 17 261.

* cited by examiner

*Primary Examiner*—Leon B. Lankford, Jr.
(74) *Attorney, Agent, or Firm*—Winston & Strawn LLP

(57) ABSTRACT

The present invention relates to improved continuous (immortalized) cell lines, in particular keratinocytes and melanocytes derived from normal human skin tissue. The present invention also relates to novel serum-free media for isolating, producing and maintaining said improved continuous keratinocyte and melanocyte cell lines. The present invention also relates to methods for producing primary melanocytes and keratinocytes under serum-free conditions without any feeder cells.

16 Claims, 3 Drawing Sheets

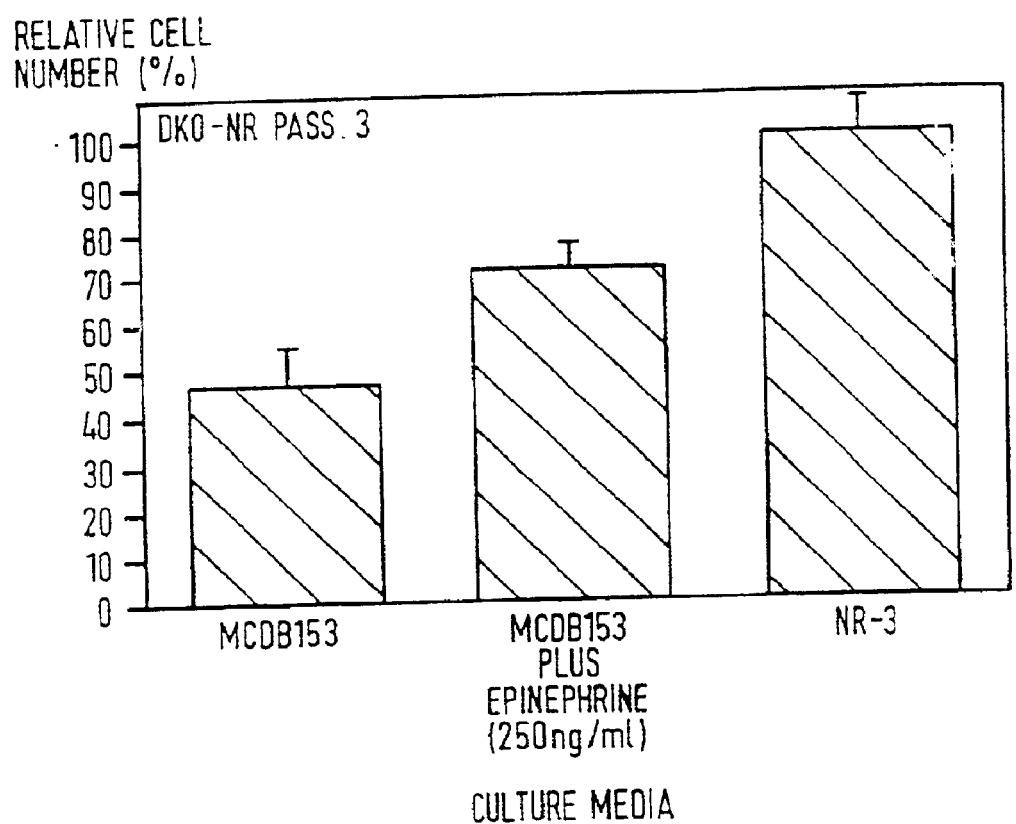

IMMORTALIZED HUMAN SKIN CELL LINES AND NOVEL SERUM-FREE MEDIUM USEFUL FOR THE PRODUCTION THEREOF

This application is a continuation of application Ser. No. 09/091,483 filed Jun. 19, 1998, now U.S. Pat. No. 6,423,540 which is a 371 of PCT/EP96/05812 filed Dec. 19, 1996 which is a continuation of application Ser. No. 08/576,483, filed Dec. 21, 1995 now abandoned.

The present invention relates to improved continuous (immortalized) cell lines derived from normal human skin tissues, in particular keratinocytes and melanocytes which retain the ability to express differentiation proteins characteristic of differentiated melanocytes or keratinocytes, even in high passages. The present invention also relates to novel serum free media which do not require the use of feeder cells.

BACKGROUND OF THE INVENTION

The production of immortalized cell lines derived from human skin tissues has been previously described. In general such methods comprise transfection or transformation of human skin cells, e.g., keratinocytes and melanocytes, cultured in vitro with agents which provide for immortalization.

Immortalization refers to the production of cells which are able to be cultured for prolonged time periods in vitro, ideally indefinitely. These cells are also referred to as continuous cell lines. By contrast non-immortalized cells are only capable of growing for a finite number of cell divisions in vitro. Immortalized cells are highly desirable because they provide a stable, potentially infinite supply of cells having defined characteristics. Conventional agents for producing immortalized cell lines and immortalized human skin cell lines in particular include, e.g., viruses, recombinant viruses, and plasmids which contain DNA sequences which provide for immortalization.

Probably the most common method of producing immortalized human cell lines involves the use of SV40 sequences and more specifically the SV40 large T antigen DNA as an immortalizing agent. For example, Steinberg et al., *J. Cell Phys.*, 123:117–125 (1985); Reddel et al., U.S. Pat. No. 4,885,238 issued on Dec. 5, 1989; Major, U.S. Pat. No. 4,707,448 issued on Nov. 17, 1987; Stoner et al., *Cancer Res.*, 51:365–371 (1991); Chopra et al., *In Vitro Cell Dev. Biol.*, 30A:539–546 (1994); Chopra et al., *In Vitro Cell Dev. Biol.*, 27A:763–765 (1991); Christian et al., *Cancer Res.*, 47:6066–6073 (1987); Rhim et al., *Science*, 227:1250–1252 (1985); and Grubman et al., *Gastrointest. Liver Physiol.*, 29:G1060–G1070 (1994) teach the use of SV40 vectors and SV40 large T antigen sequence containing vectors to produce immortalized human cell lines. The introduction of such sequences is generally effected by infection using SV40 virus or with a hybrid adenovirus-12 SV40 hybrid virus or by transfection of cells with a recombinant plasmid containing the Rous sarcoma virus long terminal repeat and the Ori-SV40 early region by strontium phosphate co-precipitation. (See Brash et al., *Mol. Cell Biol.*, 7:2031–2034, (1987)).

Another known method for producing immortalized cell lines, and immortalized human keratinocytes in particular, involves transfection or infection of cells with human papillomavirus DNA sequences. For example, U.S. Pat. No. 5,376,542 by Schlegel issued on Dec. 27, 1994 describes immortalization of human epithelial cells with isolated HPV-16, 18, 31, 33 or 35 E6 and E7 genes or the E7 gene alone to produce non-tumorigenic immortalized cell lines. Also, Barbosa et al., *Oncogene*, 4:1529–1532 (1989); and Münger et al., *J. Virol.*, 63(10):4417–4421 (1989) teach the use of HPV-16 and HPV-18 E6 and E7 genes to produce immortalized human keratinocytes.

However, while numerous groups have reported immortalized keratinocyte cell lines, and their usage in in vitro assays, previous immortalized keratinocyte cell lines and melanocyte cell lines have typically exhibited one or more properties which render their usage disadvantageous. For example, previously reported immortalized keratinocytes have exhibited one or more of the following characteristics: (i) reduction or loss of expression of differentiation markers, e.g., proteins which are expressed by normal differentiated keratinocytes, and (ii) altered growth characteristics in tissue culture.

For example, Jetten et al, *J. Invest. Dermatol.*, 92:203–209 (1989) reports SV40 immortalized keratinocytes obtained after high passage number (>passage 12) using the vector NHEK-SV40-T8-1 which are unable to differentiate. Similarly, Bernard et al, *Cancer Res.*, 45:1707–1716 (1985) report isolation of an immortalized keratinocyte cell line referred to as SVK14 which is reported to be almost completely unable to differentiate. Also, this cell line shows no expression of keratins K1/10 (>53 kD) and the 50 kD keratin (keratin K14), which proteins are normally expressed by differentiated keratinocytes.

Still further, Steinberg et al, *J. Cell. Physiol.*, 123:117–125 (1985) report SV40 transformed keratinocytes which gradually lose the ability to express keratins which are characteristic of the normal keratin cytoskeleton. This loss of normal keratin expression occurs after about 10–15 passages. Also, Hronis et al, *Cancer Res.*, 44:5797–5804 (1984) teach SV40 DNA immortalized keratinocytes which have lost the ability to produce K5, K6, K14/15, K16 and K17 keratins and involucrin which proteins are characteristic of normal differential keratinocytes. Still further, Morris et al, *Proc. Natl. Acad. Sci. USA*, 82:8498–8502 (1985) teach SV40 immortalized keratinocytes which at higher passages (>passage 14) exhibit highly reduced expression of Class II and Class I keratins. For example, these keratinocytes exhibit almost no expression of K13 (Id.).

Also, Banks-Schlegel et al, *J. Cell. Biol.*, 96:330–337 (1983) disclose SV40 immortalized keratinocytes which exhibit altered growth characteristics in tissue culture. For example, unlike normal keratinocytes, these immortalized cells require a 3T3 feeder layer to grow.

Previously described methods for producing immortalized human keratinocytes and melanocytes have typically used the feeder cell technique (wherein fibroblasts usually function as the "feeder" cells) and generally culture cells in serum-containing medium. For example, Sexton et al., "Stable transfection of human keratinocytes: HPV immortalization," Keratinocyte Methods, eds., Leigh, I. M. et al., University Press, 179–180, (1994); Garlick, "Retroviral Vectors," Keratinocyte methods, (eds. Leigh I. M. et al., Cambridge University Press, 181–183 (1994)) teach the use of fetal calf serum containing medium and feeder cells in the isolation and production of immortalized keratinocytes.

The use of serum-free medium during the isolation and production of immortalized epithelial cells, and specifically human keratinocytes has been previously described. For example, Barbosa et al., *Oncogene*, 4:1529–1532 (1989) describe initially culturing human keratinocytes transfected by electroporation or lipofection in low calcium, serum-free medium until confluence.

However, notwithstanding what has been previously reported, there still exists a significant need in the art for immortalized human keratinocytes and melanocytes which possess improved properties, in particular which maintain the differentiation potential of normal keratinocytes and melanocytes and which express differentiation proteins characteristic of differentiated melanocytes and keratinocytes, even after high passages. Such cells would be highly beneficial for many usages, in particular in assays which require differentiated skin cells. There further exists a need in the art for improved culture media capable of maintaining primary and immortalized keratinocytes and melanocytes, as well as improved culturing methods which do not require the use of feeder cells.

OBJECTS OF THE INVENTION

Towards that end, it is an object of the invention to produce improved continuous (immortalized) cell lines derived from normal human skin tissue, especially immortalized keratinocytes and/or melanocyte cell lines derived from normal human skin tissue which maintain the ability to differentiate and to express differentiation proteins even after high passages. More specifically, it is an object of the invention to obtain immortalized keratinocytes which maintain the ability to express keratins, cytochromes, as well as other differentiation proteins, e.g., involucrin, filaggrin and loricrin, which are either not expressed or poorly expressed by conventional immortalized keratinocyte cell lines. It is still another object of the invention to obtain immortalized keratinocytes and melanocytes which express enzymes which are normally expressed by differentiated keratinocytes and melanocytes, especially phase II enzymes such as glutathione-S-transferases as well as enzymes and/or proteins which are involved in cellular oxidation and inflammatory responses.

It is another object of the invention to provide novel serum free media for culturing, producing and maintaining normal or continuous keratinocytes and/or melanocytes in tissue culture. These novel serum free media are also useful for isolating, establishing and immortalizing human skin cells for obtaining continuous melanocytes and keratinocytes according to the invention. It is thus a specific object of the invention to provide a fully defined culture medium (without unknown or ill-defined supplements) for culturing keratinocytes without feeder cells containing epinephrine which has surprisingly been discovered to be a strong growth potentiator of normal keratinocytes in serum-free medium.

It is another object of the invention to provide a novel method for isolating, establishing and immortalizing human skin cells for obtaining continuous melanocyte and keratinocyte cell lines derived from normal skin tissue, said method using serum-free media, notably those according to the invention, and a cell attachment cocktail containing fibronectin, BSA and type I collagen without "feeder cells" (e.g., fibroblasts).

It is another object of the invention to provide primary keratinocyte or melanocytes produced under serum free conditions without the use of any feeder cells, said primary keratinocytes and melanocytes being used for skin grafting and in ex vivo genetic therapy.

It is another object of the invention to provide methods of using such novel and improved continuous keratinocyte and melanocyte cell lines, e.g., for immunological, pharmacological, photo- and chemotoxicological skin reaction assays and for the expression of heterologous genes.

BRIEF DESCRIPTION OF THE FIGURES

FIG. 1 compares the growth (in terms of cell number) of non-immortalized DKO-NR keratinocytes in three different media, i.e., NR-3, epinephrine-supplemented modified MCDB 153 and MCDB 153 after 6 days.

DETAILED DESCRIPTION OF THE INVENTION

Figure 2A:
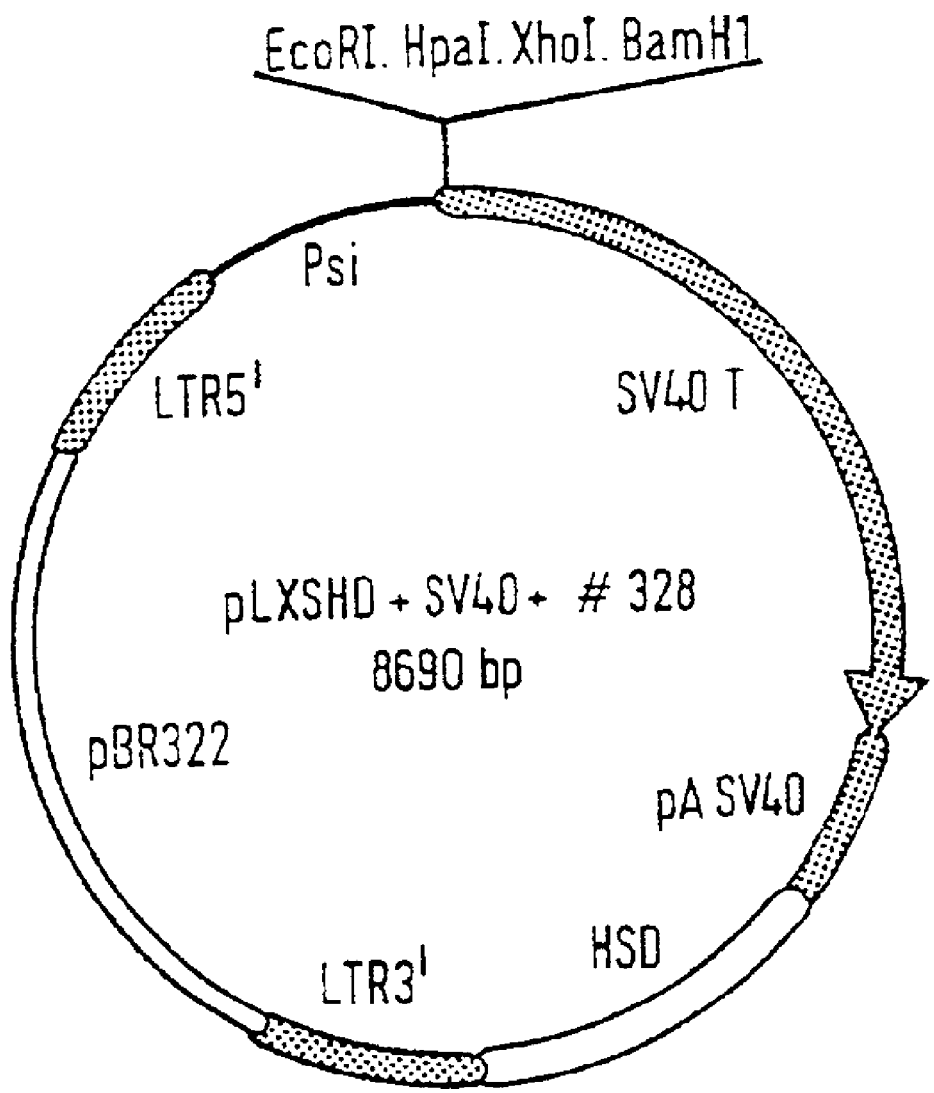
FIG. 2a depicts the SV40 retroviral construct pLXSHD+SV40(#328) preferably used to immortalize the subject melanocytes and/or keratinocytes

The present invention provides continuous (immortalized) cell lines derived from normal human skin tissues, i.e., immortalized keratinocytes and melanocytes, which maintain the ability to differentiate and which maintain the ability to express differentiation proteins which are expressed by normal keratinocytes or melanocytes even in high passages. By high passage is meant at least 10 passages in culture, preferably at least 20–30 passages, more preferably for at least 50 passages, and ideally for an infinite number of passages. For example, immortalized keratinocytes produced according to the invention express the differentiation proteins keratin K1/10, keratin K14, involucrin, filaggrin and loricrin even after high passages in tissue culture. This is in contrast to previously reported immortalized keratinocytes which either do not express these differentiation proteins or which express these differentiation proteins poorly.

Also, the present invention provides primary keratinocytes and melanocytes produced under serum free conditions and without feeder cells which maintain the ability to differentiate and to express proteins characteristic of differentiated melanocytes and keratinocytes.

The subject immortalized keratinocytes have a cytochrome p450 profile (CYP450) which is similar if not identical to that of normal keratinocytes. For example, the subject cells express CYP450 3A5 and not CYP450 3A4. Also, the subject immortalized keratinocytes express phase II enzymes, e.g., glutathione-S-transferase (GST) and more specifically GSTα, GSTμ and GSTπ comparably to normal non-immortalized keratinocytes.

Further, the subject immortalized keratinocytes express proteins and enzymes involved in the cellular oxidation and inflammatory responses, e.g., superoxide dismutase (SOD), and type I collagenase and tumor necrosis factor alpha (TNFα) after treatment with phorbol esters similarly or identically to normal differentiated keratinocytes. Given these characteristics, these cell lines provide a highly stable, reproducible source of cells for immunological, pharmacological, inflammation, photo- and chemotoxicological skin reaction studies.

Further, the subject immortalized melanocytes express endogenously melanin associated proteins (see examples 14–15 hereafter).

Also, the subject immortalized keratinocyte cell lines and melanocyte cell lines when cultivated in organotypic culture form a highly stratified and polarized epithelium having cornified superficial layers (stratum corneum). This had only been previously achieved under conventional culture conditions, i.e., medium containing serum, feeder layer technique (See, e.g., Lechner et al, *Virology*, 185:536–571, 1991).

Further, the subject immortalized keratinocytes and melanocytes are obtained from normal skin under serum-free conditions and without the use of any feeder cells. In general, the subject immortalized keratinocytes and melanocytes are obtained by the following steps:

(i) obtaining a human skin tissue sample;

(ii) preparing said skin sample for culturing in vitro;

(iii) obtaining keratinocytes and/or melanocytes from said prepared skin sample and seeding said keratinocytes and/or melanocytes into a serum-free growth medium, preferably either the NR-3 medium or NR-4 (for melanocytes) (described infra) onto culture plates provided with a coating which facilitates cell attachment and cell growth, said coating comprising fibronectin, type 1 collagen and BSA.

(iv) changing the medium as necessary to optimize confluent growth of the cultured cells while continuously maintaining the coating on the culture plates;

(v) transferring the keratinocytes or melanocytes into an selection medium, preferably a serum-free medium, onto similarly precoated culture plates;

(vi) infecting the keratinocytes or melanocytes with a retroviral construct, preferably a SV40 or papilloma virus 16 based construct, such as the SV40 plasmid pLXSHD+SV40 (#328) which contains the large T antigen (T Ag) of the Simian virus 40, or the plasmid pLXSHD+E6/E7 which contains the E6/E7 gene of the papilloma virus 16 (HPV16) (described infra);

(vii) transferring the resultant immortalized keratinocytes or melanocytes to a proliferation medium suitable for proliferating immortalized keratinocytes or melanocytes onto similarly precoated culture plates, preferably NR-2 or NR-3 medium (described infra) and the melanocyte medium M2 (source M. Olsson, Inst. of Dermatology, Uppsala, Sweden); and (viii) transferring the resultant proliferated keratinocytes to a differentiation medium, preferably NR-2 (described infra) or modified MCDB 153 medium (described infra) which contains high calcium, preferably 1.5 mM onto similarly precoated culture disks (Boyce et al., J. Tissue Cult. Meth., 9:83–93, 1985; Pittlekow et al., J. Invest. Dermatol., 86:410–417, 1986).

More specifically, step (i) will typically comprise obtaining human skin tissue samples from human donors, e.g., those obtained during surgery or pediatry. The immortalization of a single skin cell sample, i.e. autologous skin cell sample, allows for the production of immortalized keratinocyte and melanocyte cell lines which exhibit defined characteristics, e.g. a particular receptor profile which is characteristic of a particular donor.

The skin sample will then be prepared in step (ii) such that it is suitable for culturing in vitro. This will preferably be effected by initially washing the skin sample, e.g. using the same medium which is used for culturing. Preferably this is effected in NR-2 medium, a serum-free medium, the exact composition of which is disclosed infra, which has been found to be advantageous for culturing normal keratinocytes and melanocytes. After washing, the skin sample will then preferably be shaved, e.g. with a dermatome, and then excised into small pieces.

The resultant skin sections are then preferably separated into dermis and epidermis. This may be effected by physical and/or enzymatic means. For example, this may be effected by trypsinization, e.g. by floating skin sheets in a trypsin solution (e.g. about 0.5%) containing EDTA (e.g. about 0.1%) for a sufficient time to effect cell separation, e.g. about 30–60 minutes at 37° C. or overnight at 4° C.

The dermis is separated (to isolate the fibroblasts, see EXAMPLE 2) and the epidermis is then placed in a suspension medium. Preferably the suspension medium will contain soybean trypsin inhibitor solution (SBTI) and will be contacted with the cells for a sufficient time, typically about 5 minutes, in order to inactivate the trypsin and provide for cell release. Tissue culture medium will then be added, preferably serum-free NR-2 medium (described infra) and a filter (e.g. 100 mm filter) to obtain the desired cells, i.e. keratinocytes and/or melanocytes.

The resultant primary keratinocyte/melanocyte culture obtained in step (ii) is then seeded into serum-free medium, preferably NR-3 medium (described in detail infra), at a suitable cell concentration, preferably about $1.2 \times 10^4$ cells/$cm^2$, onto precoated culture plates. However, this cell concentration may be varied within wide limits. The culture plates are preferably continuously coated with a composition which has been surprisingly found to enhance both the attachment and growth of keratinocytes and melanocytes, specifically a solution of fibronectin, BSA and collagen type 1. This cell coating composition has previously been described for use with bronchial cells. (Lechner et al, *J. Tissue Cult. Meth.* 9:43–48 (1985)), which reference is incorporated by reference herein.

In step (iv) the culture medium is changed as often as necessary to optimize cell growth. Preferably, the medium will be changed about every second day. However, this may vary dependent upon the particular skin sample. After reaching almost total confluence, e.g. about 90% confluence, which typically occurs after about 10–14 days, the keratinocytes and melanocytes are then separated. This may be accomplished by any means which provides for adequate cell separation without adversely affecting the melanocytes and/or keratinocytes. For example, this may be effected by differential trypsinization. Preferably, the melanocytes or keratinocytes will be treated with a trypsin/EDTA solution, and then transferred to the selection medium. In the case of keratinocytes, the cells are preferably treated for about 5–10 minutes with trypsin/EDTA solution (0.025%/0.01%) and then in step (v) seeded into NR-3 medium onto precoated plates. It is important to note that NR-3 medium promotes the growth of keratinocytes versus melanocytes. In the case of melanocytes, the cells are preferably treated for about 2–4 minutes with trypsin/EDTA (0.025%/0.01%) and then seeded in step (v) into NR-4 medium onto similarly precoated culture plates. It is important to note that NR-4 medium specifically inhibits the growth of keratinocytes.

Figure 2B:
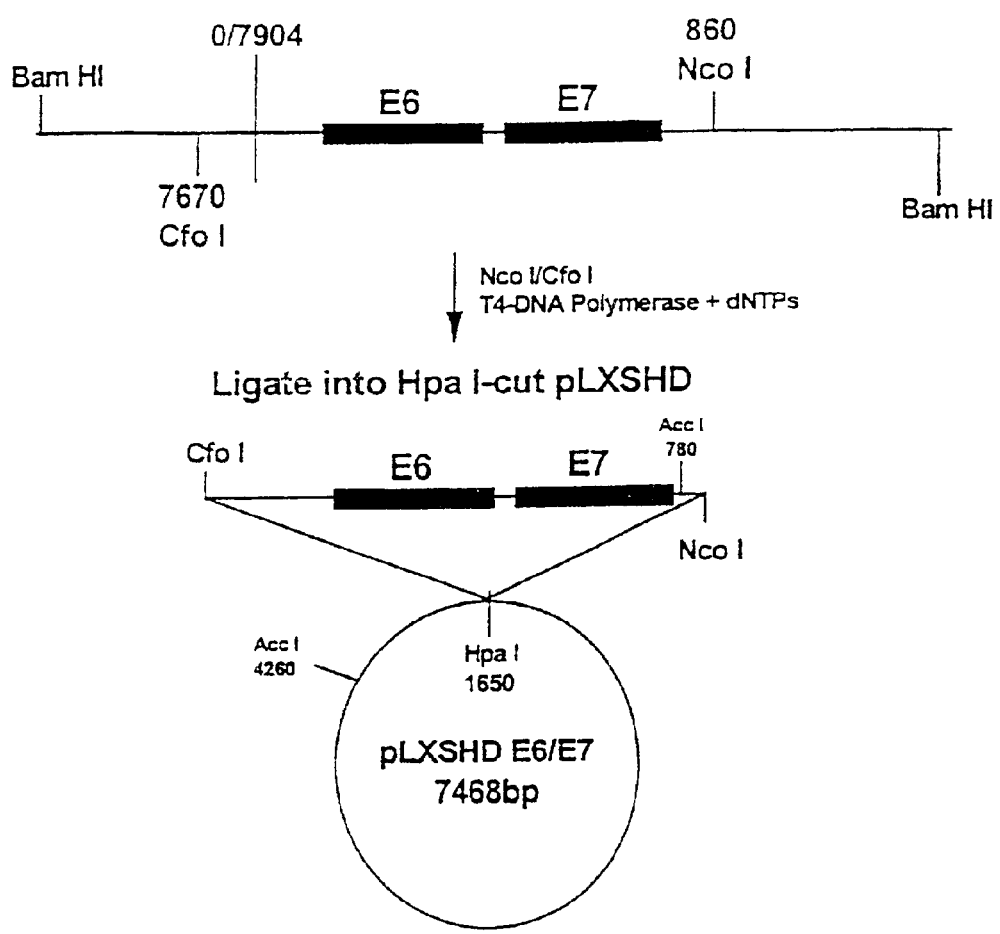
FIG. 2b depicts the HPV16 retroviral construct pLXSHD+E6/E7.

These cells will then be treated with the immortalizing agent. Alternatively, the cells may be frozen until immortalization is to be effected, e.g. in liquid $N_2$. Infection and immortalization is preferably effected using the SV40 construct identified as pLXSHD+SV40(#328) which is depicted in FIG. 2a and which was described by Stockshlaeder et al (GeneBank, n° accession M64753; Stockshlaeder et al., Human Gen. Therapy, 2, 33–39, 1991), or the HPV16 construct identified as pLXSHD+E6/E7 which is depicted in FIG. 2b. The pLXSHD+SV40(#328) construct contains the SV40 T-Ag sequence, 5' and 3' LTR sequences of SV40, pBR322 sequences which provide for replication in *E. coli,* a multiple cloning site, an SV40 polyadenylation sequence, among other sequences. The pLXSHD+E6/E7 construct contains, instead the T-Ag, the NcoI/CfoI fragment of the E6/E7 gene of the human papilloma virus 16. The method to construct the E6/E7-plasmid is based on Dürst et al. (Dürst et al. 1987, Oncogene 1:251–256). After immortalization, the cells are passaged as necessary during culturing and the resultant immortalized cells are then transferred to a proliferation medium in step (vii). In the case of keratinocytes, this transferral is preferably made at passage 2.

In step (viii) the immortalized cells are expanded in a proliferation medium for immortalized keratinocytes or melanocytes which will comprise a serum-free medium and preferably will comprise NR-2 or NR-3 and M2-medium for melanocytes (described infra). The immortalized cells are again cultured on continuously precoated culture plates, with the coating again comprising a solution of fibronectin, BSA and type 1 collagen.

After the immortalized cells are expanded in the proliferation medium, they are then transferred in step (viii) to a medium which provides for differentiation of normal and immortalized keratinocytes. Preferably, this medium will comprise NR-2 or modified MCDB 153 media containing high calcium, preferably about 1.5 mM calcium, with culturing again being effected on culture plates continuously coated with a solution of fibronectin, BSA and type I collagen.

As noted above, it has been surprisingly discovered that immortalized keratinocyte and melanocyte cell lines produced according to the subject method maintain the ability to differentiate and to express differentiation proteins which are characteristic of normal differentiated keratinocytes and melanocytes, even after high passage in tissue culture i.e. after at least 10 passages. For example, the subject immortalized keratinocytes express keratins as well as other proteins, e.g. involucrin, filaggrin, and loricrin after high passage which are either not expressed or are poorly expressed by previously reported SV40 immortalized keratinocytes.

More specifically, several immortalized keratinocytes cell lines produced according to the invention, DK2-NR, DK3-NR and FK2-NR (see Tables 7 and 8 infra) express the differentiation proteins keratin K1/10, keratin K14, involucrin, filaggrin and loricrin even after in high passages (>passage 30).

Also, immortalized keratinocytes produced according to the invention have a CYP450 profile which is similar if not identical to that of normal human keratinocytes. For example, the subject immortalized keratinocytes express CYP450 1A1, 2C, 2E1 and 3A5 but do not express CYP450 1A2, 2A6, 2B6 and 2D6 which is characteristic of the cytochrome 450 profile of normal keratinocytes. This was the first time it could be demonstrated that normal and immortalized human keratinocytes express CYP450 3A5 and not CYP450 3A4.

Also, the subject immortalized keratinocyte cell lines express phase-II enzymes, e.g. glutathione-S-transferases (GST) comparably to normal differentiated keratinocytes. More specifically, the subject immortalized keratinocyte cell lines express GSTα, GSTµ and GSTπ comparably to normal keratinocytes.

Further, the subject immortalized keratinocytes express enzymes and other proteins which are involved in cellular oxidation and inflammatory responses comparably to normal keratinocytes. For example, immortalized keratinocytes produced according to the invention express superoxide dismutase (SOD). Also, in response to phorbol esters immortalized keratinocytes produced according to the invention express type I collagenase (a mediator of inflammation) and TNF-α (tumor necrosis factor alpha).

The subject melanocytes have the capacity to express melanin associated proteins and vimentin.

Moreover, the subject immortalized cell lines when grown in organotypic culture form a highly stratified and polarized epithelium having cornified superficial layers (stratum corneum) even in higher passages (>passage 20). This has only been previously reported for immortalized keratinocyte cell lines established under conventional culture conditions, i.e. medium containing serum, and using a feeder layer.

The subject immortalized cells lines are obtained under total serum-free conditions without the use of any feeder layers during culturing.

Moreover, as described in greater detail infra, it has been surprisingly discovered that epinephrine is a strong growth factor of normal keratinocytes when used in serum free medium. Specifically, the NR-3 medium described infra contains epinephrine which has been found to enhance the growth of normal keratinocytes (see FIG. 1). This is quite surprising given the fact that epinephrine has previously been reported to inhibit the growth of keratinocytes (Halprin, *J. Invest Dermatol.*, 81:553–557 (1983)) or to only have a moderate effect on keratinocyte cell growth (Koizumi et al, *J. Invest. Dermatol.*, 96:234–237, 1991).

Also, it has been surprisingly discovered that the continuous coating of the culturing dishes or plates used to culture primary and immortalized keratinocytes and/or melanocytes, in particular with a coating or "cocktail" containing fibronectin, BSA and type I collagen improves both the attachment of keratinocytes and melanocytes to culture plates or culture dishes, as well as enhancing cell growth. The use of such a coating material has not been previously described for use with immortalized keratinocytes and/or melanocytes.

As discussed, the present invention further specifically provides a novel serum-free medium referred to as the NR-3 medium. This medium allows for culturing and isolation of normal keratinocytes and/or melanocytes from human skin under serum-free conditions without the use of a feeder layer. This medium has been found to improve the growth of normal keratinocytes and to allow the establishment of normal keratinocyte cultures without any contact with serum or feeder cells.

The exact composition of the NR-3 medium is described in Table 1. This medium contains various amino acids, inorganic salts as trace elements, vitamins, growth factors and other substituents. For example, this medium contains as growth factors epidermal growth factor (EGF recombinant), insulin, hydrocortisone, transferrin (human), bovine pituitary extract, and epinephrine. As noted, epinephrine has surprisingly been discovered to enhance the growth of primary keratinocytes in tissue culture.

As amino acids this medium contains L-alanine, L-arginine-HCl, L-asparagine-$H_2O$, L-aspartic acid, L-cysteine-HCl-$H_2O$, L-glutamic acid, glutamine, glycine, L-histidine-HCl-$H_2O$, L-isoleucine, L-leucine, L-lysine-HCl, L-methionine, L-phenylalanine, L-proline, L-serine, L-threonine, L-tryptophan, L-tyrosine and L-valine.

The inorganic salts contained therein are ammonium metavanadate, ammonium molybdate, calcium chloride, cupric sulfate, ferric sulfate, magnesium chloride, manganese chloride, nickel sulfate, potassium chloride, sodium acetate, sodium bicarbonate, sodium chloride, sodium phosphate dibasic, sodium pyruvate, sodium selenite, sodium silicate, tin chloride and zinc sulfate.

The vitamins contained in the NR-3 medium are d-biotin, d-calcium pantothenate, choline chloride, cyancocalbumin, folic acid, i-inositol, nicotinamide, pyridoxine and riboflavin.

The medium further contains adenine, ethanolamine, phosphoethanolamine, phenol red Na, putrescine 2HCl, thiamine HCl, thioctic acid, thymidine, glucose, HEPES and antibiotics (fungizone, penicillin and streptomycin).

The preferred composition of the NR-3 medium is described in Table 12. However, it is expected that the concentration of the substituents contained in the NR-3 medium may be varied within wide limits. More particularly, it is expected that the amounts of the various substituents may be varied ±50 to ±0.1%, more preferably from ±10 to ±0.1% from the concentrations disclosed in Table 12. Moreover, it is expected that one or more of the recited substituents may be deleted and other substituents may be added provided that such substituents do not substantially adversely affect the isolation and establishment of keratinocyte or melanocyte primary cell cultures and immortalized cell lines. This can be determined by one skilled in the art by trial and error analysis.

As noted, a significant substituent of the subject NR-3 serum-free medium is epinephrine. It has been discovered that epinephrine has a very strong growth promoting activity on primary human keratinocytes.

The reason that epinephrine enhances proliferation of keratinocytes is unclear. It has been reported that human keratinocytes express enzymes for epinephrine synthesis and also express at high density beta 2-adrenoreceptors (Schallreuther et al., "Production of catecholamines in the human epidermis," *Biochem. & Biophys. Res. Commun.*, 189:72–78 (1992)). These enzymes are involved in the catecholamine biosynthetic pathway, in particular phenylethanolamine-N-methyltransferase and biopterin dependent tyrosine hydroxylase. By contrast, such enzymatic activity cannot be detected in melanocytes and fibroblasts. Accordingly, this enzymatic activity and/or receptor expression may explain the ability of epinephrine to modulate the proliferation of keratinocytes.

It is hypothesized by the present inventors that the NR-3 medium enhances the isolation and establishment of primary cell cultures and cell lines because it suppresses cell differentiation which leads to an enrichment of cells which maintain their ability to differentiate and to express proteins and enzymes expressed by normal differentiated keratinocytes and melanocytes.

More specifically, it is believed that the growth of keratinocytes or melanocytes in serum containing medium favors differentiation in the first passage. However, this is disadvantageous (during the initial culturing period) because differentiated cells do not grow well. This in turn results in the overgrowth and selection of proliferative skin cells which only possess a weak capacity to differentiate. Consequently, the number of cells which possess high differentiation capacity are reduced if serum is added to the medium prior to immortalization.

By contrast, in the present invention the keratinocytes and melanocytes are cultured in a serum-free medium and under conditions which inhibit the differentiation of melanocytes and keratinocytes. In the present invention, serum-free medium is preferably used during the entire cultivation period both prior to and during immortalization, as well as during proliferation and differentiation.

As noted, the subject NR-3 serum-free culture medium inhibits differentiation of keratinocytes and thereby allows for improved isolation of keratinocyte primary cell cultures and immortalized cell lines derived therefrom. Moreover, this serum-free medium contains low calcium concentrations which inhibits selectively the growth of co-isolated fibroblasts. This results in a highly selective growth medium which favors the production of cultures which predominantly contain melanocytes and keratinocytes. Accordingly, the subject serum-free NR-3 medium is advantageous because it inhibits keratinocyte differentiation and also inhibits fibroblast growth.

As discussed, a cell suspension produced from a single skin sample which contains dissociated melanocytes, keratinocytes and fibroblasts will preferably be cultured in the subject NR-3 medium. This will be effected by seeding such cells onto culture dishes which are continuously coated with a composition which facilitates their attachment. Preferably, this coating will comprise a mixture of fibronectin, bovine serum albumin and type 1 collagen. This coating or "cocktail" coating has been previously described for bronchial cells (Lechner et al., *J. Tiss. Cult. Meth.*, 9:43–48 (1985)). The present inventors have found that this cocktail also enhances the attachment of keratinocytes and melanocytes to plastic culture dishes. Moreover, it has been surprisingly found that said continuous coating of culture plates which are used to culture primary and immortalized keratinocytes further improves cell growth. The continuous coating of culture plates has not been previously described for immortalized keratinocytes or melanocytes.

During culturing the primary cell cultures are preferably split when they reach or substantially reach confluence, and then expanded onto other coated culture dishes. Typically, cell cultures will be divided about every 10 to 14 days.

After the primary melanocytes and/or keratinocytes have been cultured and expanded to desired cell numbers in NR-3 serum-free medium using the described coated culture dishes they are then immortalized. Preferably, the melanocytes and keratinocytes which exhibit the best growth are immortalized. However, alternatively the expanded primary melanocytes or keratinocytes may be used prior to immortalization, e.g., in assays, skin grafting or in gene therapy.

Immortalization of both melanocytes and keratinocytes may be effected with a vector which provides for the expression of the SV40 T-antigen or for the expression of the E6/E7 gene of human papilloma virus 16 (HPV16). Preferably, immortalization is effected by infection of melanocytes or keratinocytes with a retroviral construct which provides for the expression of the SV40 T-antigen or E6/E7 gene of HPV16. The cellular T-Ag infection is based following the protocol of Pfeifer et al. Meth. Cell Sci. 17: 83–89, 1995 (except virus was collected from packaging cell line forwing in DMEM, 10% fetal calf serum). During infection, serum containing medium may be used. However, serum free medium is preferred for melanocytes and keratinocytes, preferably, e.g., the PC-1 medium described in the paper of Pfeifer et al., *Meth. Cell. Sci.*, 14, 83–89 (1995), which reference is incorporated by reference herein. Most preferably, immortalization is effected using the retroviral construct referred to as pLXSHD+SV40(#328) shown in FIG. 2a, and based on Pfeifer et al. and Stockshlaeder et al. (GeneBank, n° accession M64753), or as pLXSHD+E6/E7 shown in FIG. 2b and based on Dürst et al. 1987, Oncogene 1, 251–256.

After immortalization the immortalized cell lines are transferred to a proliferation medium, preferably NR-2 or NR-3, or M2 (for melanocytes) using precoated culture dishes. After the cells are proliferated to desired cell numbers, the cells are transferred to a differentiation medium suitable for culturing normal and immortalized keratinocytes. Preferably, this will comprise NR-2 or modified MCDB 153 with high calcium (1.5 mM) or M2 (for melanocytes) using precoated cultured plates (the same BSA, type I collagen, fibronectin coating).

As noted previously differentiated immortalized keratinocyte and melanocyte cell lines produced according to the invention exhibit improved properties which render these cell lines well suited for use in assays which require differentiated human skin cells. In particular, these cell lines have been found to express proteins characteristic of normal differentiated melanocytes and keratinocytes even after high passages.

For example, when immortalized keratinocytes produced according to the invention are assayed by Western blot and RT-PCR, they possess a cytochrome p450 (CYP450) profile similar if not identical to normal keratinocytes. More specifically, immortalized keratinocytes produced according to the invention express CYP450 1A1, 2C, 2E1, 3A5 and do not express CYP450 1A2, 2A6, 2B6 and 2D6. This CYP450 profile is consistent with normal keratinocytes. Such a metabolism profile has not previously been described for immortalized keratinocytes. Indeed, this is the first time it could be demonstrated that normal and immortalized keratinocytes express CYP450 3A5 and not CYP450 3A4. Also, immortalized keratinocytes produced according to the invention, when analyzed using antibodies specific for differentiation markers, are found to express other differentiation proteins even after high passage. More particularly, the subject cell lines express the differentiation proteins K1/10, keratin K14, involucrin, filaggrin and loricrin even at high passages, i.e. after 10 passages and substantially greater.

The subject, immortalized keratinocytes and melanocytes also uptake exogenous essential fatty acids (EFA) and exhibit desaturation and chain elongation of EFA highly consistent to normal melanocytes and keratinocytes.

Further, as described in greater detail infra, the subject immortalized keratinocytes express TNFα and the inflammation mediator collagenase type I, when treated with phorbol esters comparably to normal keratinocytes. Also, the subject immortalized keratinocytes express superoxide dismutase, an enzyme involved in cellular oxidation similar to normal differentiated keratinocytes.

Also, immortalized melanocytes produced according to the invention treated with melanogenesis inducers (e.g., theophylline and tyrosine) and melanogenesis inhibitors (kojic acid) respond similarly to normal melanocytes.

Given these properties, the subject immortalized keratinocytes and melanocytes are well suited for immunological, pharmacological, photo- and chemotoxicological skin reaction studies.

For example, the subject immortalized keratinocyte and melanocyte cell lines and primary melanocytes and keratinocytes may be used in assays which require differentiated skin cells, e.g., barrier-function studies (cornification) of reconstructed skin, metabolism studies of differentiated keratinocytes (fatty acid metabolism, antioxidant metabolism), studies relating to effects of ultraviolet radiation on skin cells, studies relating to the effects of potential skin irritants and sensitizers on skin cells, assays measuring the effects of compounds on melanin production, lipid-metabolism studies, topical treatment with xenobiotics (e.g., cosmetic oils, screening for putative protective compounds, e.g., photoprotectors), skin inflammation and irritation studies, etc.

Also, immortalized keratinocyte and melanocyte cell lines and primary melanocytes and keratinocytes produced according to the invention are useful for screening potential anti-cancer treatment compounds and skin disease treatment compounds. This will typically involve exposing the cell line or primary cells to such compounds for a period of time and ascertaining whether they induce any adverse effects, e.g., genotoxicity, DNA adduct formation, mutagenicity, cell transformation or cytotoxicity.

Also, the subject melanocyte and keratinocyte cell lines are suitable for the expression of recombinant proteins, e.g., human proteins and polypeptides, as well as for the production of RNA and DNA.

Further, the subject immortalized cell lines have potential utility for ex vivo genetic therapy. The subject cell lines should provide a useful tool for genetic targeting and developing genetically engineered cells which express desired gene products, e.g., for therapeutic application, or for cell toxicity/mutagenicity studies. Moreover, given the fact that the subject cell lines closely mimic normal skin cells they should be well suited for biosensitivity assays.

Additionally, primary keratinocytes and melanocytes produced according to the subject invention, given that they are produced under serum-free conditions, may be useful in gene therapy. Essentially, because these cells are not exposed to serum, e.g., bovine or other animal serum (except for during viral infection and storage in liquid nitrogen), they should be less subject to potential contamination by viruses or other pathogenic agents. Therefore, this should minimize the risk of these cells transmitting pathogenic or infective factors during gene therapy. Such ex vivo genetic therapy has potential in the treatment of disorders such as Epidermolysis bullosa (keratin mutation disorder), Vitiligo (a disorder involving melanin synthesis genes), carcinomas and melanomas, allergic disorders and inflammation related disorders. With respect to therapeutic treatment, the only potential source of contamination is the bovine pituitary extract, bovine insulin, bovine collagen, bovine serum albumin or human fibronectin and human transferrin.

Also, the subject immortalized melanocyte and keratinocyte cell lines and primary melanocytes and keratinocytes have utility in DNA mutagenesis assays, skin mutagen screening assays, assays for identifying chromosome damaging agents, malignant transformation studies, cellular biochemistry studies (e.g., CYP450 activation assays), screening of compounds and compositions, e.g., essential fatty acid cocktails which are involved in inflammation and allergic reactions, collagenase activation assays (related to inflammation), involving TNFα, interleukin detection.

A significant potential application of primary keratinocytes or melanocytes produced according to the invention, given their availability and method of production, is for skin grafting. Because these primary keratinocytes and melanocytes are produced under serum-free conditions, they should pose minimal risk of being contaminated by pathogens (e.g. viruses) and infectious agents. Moreover, because the subject melanocytes and keratinocytes may be derived from an autologous host, i.e., a patient having a large wound, this should minimize or eliminate the risk of rejection of the skin graft, or other adverse immunological reaction, as well as minimizing the risk of infection.

Examples of specific immortalized keratinocyte cell lines produced according to the invention are FK2-NR, DK2-NR and DK3-NR which were deposited on Oct. 5, 1995, at DSM-Deutsche Sammlung von Mikrorganismen Und ZellKulturen GmbH, which address is Mascheroder Weg 1b D-38124 Branschweig Germany, and which have respectively been accorded Accession Nos. DSM ACC2240, DSM ACC2238, and DSM ACC2239. Furthermore examples of specific immortalized human melanocyte lines produced according to the invention is DM2-NR which is deposited on Dec. 11, 1996 at the Pasteur Institut, which address is 25 rue de Docteur Roux 75724 Paris France, and which has been accorded Accession No CNCM I-1796. These deposits were made in accordance with the Budapest Treaty. All restrictions as to the availability of these cell lines will be irrevocably withdrawn upon issuance of a patent to this application or another application which claims benefit of priority to this application.

Other features of the invention will become apparent in the course of the following descriptions of exemplary embodiments which are given for illustration of the invention and are not intended to be limitative.

EXAMPLE 1

Characterization of Established Skin Cells

Table 1 lists all skin samples which were processed for viral infection. The isolated keratinocytes which show the best cell growth were used for immortalization.

TABLE 1

Skin Samples Used for Cell Isolation in NR-3-Medium

| Origin of Tissue | Name of Cell Strain | Age | Sex | Cell Growth[1] |
|---|---|---|---|---|
| thigh | OS1 | 36 | f | ++ |
| thigh | OS2 | 68 | f | − |
| thigh | OS3 | 51 | f | + |
| eyelid | EL1 | 46 | f | + |
| eyelid | EL2 | 49 | f | + |
| abdomen | Thor1 | 58 | f | − |
| foreskin | FK1-NR | 5 | m | +++ |
| foreskin | FK0-NR | 13 | m | ++++ |
| abdomen | GK0-NR | 26 | f | +++ |
| breast | DK0-NR | 29 | f | +++ |

[1]Method: Cells were harvested in trypsin/EDTA (0.05%/0.01%) and counted by using a hemocytometer, the results are the mean of triplicates.

Human fibroblasts were isolated from the skin samples FKO-NR, GKO-NR, DKO-NR. After the separation of the dermal and epidermal compartment the dermis was cut into small pieces 0.2×0.2 mm and fixed on a 6cm culture plate with serum. Dulbecco's minimal essential medium (DMEM, 10% FCS) was added after 2–4 hours. This explant culture was then incubated until fibroblast outgrowth was visible. Confluent fibroblast cultures were split and expanded for frozen stocks.

EXAMPLE 2

1) Characterization of Keratinocytes Growth in Serum-free Media: primary cell cultures were cultivated in modified MCDB 153 [Boyce et al., *J. Tissue Cult. Meth.*, 9:83–93 (1985); and Pittlekow et al., *J. Invest. Dermatol.*, 86:410–417, 1986] and NR-3 media. The best cell growth has been observed in NR-3 medium (FIG. 1). Improved cell growth has been also observed in fully defined NR-3 medium (NR-3 without bovine pituitary extract, BPE) compared to modified MCDB 153 without BPE.

FIG. 1 comprises cell growth in NR-3 and epinephrine-supplemented modified MCDB 153 (keratinocyte growth medium) after 6 days. The modified MCDB 153 medium refers to modified MCDB 153. Keratinocytes were harvested in trypsin/EDTA (0.05%/0.01%) and counted by using a hemocytometer. The results shown in FIG. 1 are the mean of triplicates.

2) Effect of Coating on Cellular Attachment and Cell Growth: the coating of culture plates was found to improve the cell attachment and the cell growth of normal keratinocytes. In particular, the results shown in Table 2 compare the growth of keratinocytes in coated and uncoated culture plates. 100,000 keratinocytes were seeded on 3.5 cm plates containing NR-3 medium.

TABLE 2

Effect of Surface Coating on the Cell Attachment

| | attached cells 24 h after seeding[1] | | cell number after 4 d[2] | |
|---|---|---|---|---|
| | uncoated % | coated % | uncoated | coated |
| DK0-NR after isolation | 21.4 | 68.2 | 44600 | 143800 |
| DK0-NR passage 2 | 73.8 | 86.8 | 175500 | 282300 |

[1]Number of cells attached divided by the number of cells inoculated. Attached cells were harvested in trypsin/EDTA (0.05%/0.01%) and counted by using a hemocytometer.
[2]Cells were harvested in trypsin/EDTA (0.05%/0.01%) and counted by using a hemocytometer, the results are the mean of triplicates.

EXAMPLE 3

1) Immortalization of Keratinocytes: a cell suspension produced from skin samples described in example 1, which contains dissociated melanocytes, keratinocytes and fibroblasts, are cultured in the subject NR-3 medium. This is effected by seeding such cells onto culture dishes which are continuously coated with the "cocktail" coating previously described for bronchial cells (Lechner et al., *J. Tiss. Cult. Meth.*, 9:43–48 (1985)). During culturing the primary cell cultures when they reach or substantially reach confluence, the cells are treated for 4 min with trypsin/EDTA (0.025%/0.01%). During this treatment, the melanocytes detached from the keratinocytes culture, and they are collected separatly. Primary melanocytes and keratinocytes are thus separated at this stage. After the primary keratinocytes have been cultured and expanded to desired cell numbers in NR-3 serum-free medium using the described coated culture dishes (promotes the growth of keratinocytes versus melanocytes) they are then immortalized. Immortalization of keratinocytes is effected with the retroviral construct pLXSHD+SV40 (#328) which provides for the expression of the SV40 T-antigen (see Pfeifer et al. Meth. Cell Sci. 17: 83–89, 1995; except virus was collected from packaging cell line forwing in DMEM, 10% fetal calf serum). During infection, the PC-1 serum free medium described in the paper of Pfeifer et al., *Meth. Cell. Sci.*, 14, 83–89 (1995), is used. After immortalization the immortalized cell lines are transferred to the NR-2 or NR-3 proliferation medium using precoated culture dishes. After the cells are proliferated to desired cell numbers, the cells are transferred to a differentiation medium suitable for culturing normal and immortalized keratinocytes.

2) Cell Proliferation of Immortalized Keratinocytes in High Passages: the immortalized keratinocytes were demonstrated to exhibit improved cell growth in high passages. This is shown in Table 3 below. This was demonstrated by the estimation of the population doubling time (PDT: time for one doubling of the cell population during the logarithmic growth phase). Method: Keratinocytes were harvested in trypsin/EDTA (0.05%/0.01%) and counted by using a hemocytometer, the results are the mean of triplicates.

TABLE 3

Population Doubling Time (PDT) of Keratinocyte Lines Grown in NR-3

| Keratinocytes | passage number | PDT (h) | crisis* in passage |
|---|---|---|---|
| FK2-NR | 15 | 48.00 | 16–18 |
| FK2-NR | 39 | 21.16 | |
| DK1-NR | 12 | 23.20 | 25–30 |
| DK1-NR | 15 | 31.05 | |
| DK1-NR | 31 | 32.99 | |
| DK2-NR | 15 | 22.26 | 20–21 |
| DK3-NR | 40 | 24.34 | — |

*Crisis: cell growth with reduced proliferation rate.

3) CYP450-expression in Immortalized Human Keratinocyte lines: CYP4501A1, 1A2, 3A5, 2E1, 2B6, 2A6, and 2D6 expression were analyzed in normal and immortalized keratinocytes skin cells by Western blot (protein-expression) and RT-PCR (mRNA-expression, see Table 4). The expressed CYP450 in immortalized keratinocytes is similar to normal keratinocytes. The rate of expression is slightly reduced. However the DK2-NR-line shows almost a normal rate of CYP450-expression. Method: RT-PCR (reverse transcriptase-polymerase chain reaction) with specific primer for CYP450 (Macé et al. in preparation).

TABLE 4

CYP mRNA Expression in Human Keratinocytes

| Keratinocytes | Passage number | 1A1* | 2C** | 2E1 | 3A5 | 1A2, 2A6 2B6, 2D6 |
|---|---|---|---|---|---|---|
| FK0-NR | 4 | + | + | + | + | − |
| FK2-NR | 36 | + | + | + | + | − |
| DK0-NR | 3 | + | + | + | + | − |
| DK1-NR | 31 | + | + | + | + | − |
| DK2-NR | 13 | + | + | + | + | − |

*1A1 mRNA expression in immortalized cell lines was increased after induction with Benz(a)pyrene (1.5 μm; Amersham Inc.). The increase was comparable to normal cells
**2C17/19 and 2C18

4) Response to CYP450-Inducers: the cell lines respond to the CYP450-inducer Benz(a)pyrene like non-immortalized cells even in high passages (see Table 5). This induction is not described for T-Ag immortalized keratinocytes.

TABLE 5

7-ethoxyresorufin O-deethylase (EROD; Sigma Inc.) Activity In Human Keratinocytes after Induction with Benzpyrene (B(a)P)*

| Keratinocytes | passage number | EROD (pmol/mg protein) |
|---|---|---|
| FK0-NR | 2 | undetectable |
| FK0-NR + B(a)P | 2 | 0.58 |
| FK2-NR | 37 | 0.01 |
| FK2-NR + B(a)P | 37 | 1.05 |
| DK0-NR | 1 | 0.02 |
| DK0-NR + B(a)P | 1 | 1.03 |
| DK1-NR | 32 | 0.04 |
| DK1-NR + B(a)P | 32 | 1.78 |
| DK2-NR | 14 | 0.02 |
| DK2-NR + B(a)P | 14 | 0.69 |
| DK3-NR | 39 | 0.01 |
| DK3-NR + B(a)P | 39 | 1.86 |

*Keratinocytes were incubated 24 h with B(a)P (1.5 μM). EROD activity was measured after incubation at 37° C. by fluorescence detection of resorufin product (560 nm excitation 586 nm emission).

5) Cell Differentiation: differentiation markers were analyzed using specific antibodies. The specific antibodies used are identified in Table 6. The highest differentiation capacity could be demonstrated in DK2-NR and DK1-NR clone (Tables 7, 8).

TABLE 6

Antibodies used for the Detection of Keratinocyte-Specific Proteins

| Specificity | Name of the Antibody | Company/Reference |
|---|---|---|
| T-Ag | Ab-2 | Oncogene, Manhassat, NY |
| Involucrin | BTI BT-576 | bti, Stoughton, MA |
| Filaggrin | Filaggrin | Paesel + Lorei, Frankfurt, Germany |
| Loricrin | aAg 73 | Magnaldo et al. 1992 |
| Vimentin | V9 | Dako, Glostrup, Denmark |
| Keratin K4 | 6B10 | Sigma, St. Louis, USA |
| Keratin K7 | LDS-68 | Sigma, St. Louis, USA |
| Keratin K8 | M20 | Sigma, St. Louis, USA |
| Keratin K10/1 | K8.60 | Sigma, St. Louis, USA |
| Keratin K13 | KS-1A3 | Sigma, St. Louis, USA |
| Keratin K14 | CKB1 | Sigma, St. Louis, USA |
| Keratin K17 | CK-E3 | Sigma, St. Louis, USA |
| Keratin K18 | CY-90 | Sigma, St. Louis, USA |
| Keratin K19 | A53-B/A2 | Sigma, St. Louis, USA |

TABLE 7

Detection of T-Ag and Differentiation Products of Epidermal Keratinocytes

| Keratinocyte | Passage Number | T-Ag | Involucrin | Filaggrin | Loricrin | Vimentin |
|---|---|---|---|---|---|---|
| FK0-NR | 2 | − | +++ | ++ | + | ++ |
| FK2-NR | 25 | +++ | ++ | ++ | + | ++ |
| DK0-NR | 2 | − | +++ | +++ | ++ | +++ |
| DK1-NR | 13 | +++ | +++ | ++ | ++ | ++ |
| DK1-NR | 30 | +++ | ++ | ++ | + | ++ |
| DK2-NR | 11 | +++ | +++ | +++ | ++ | +++ |
| DK3-NR | 36 | +++ | ++ | ++ | + | ++ |

TABLE 8

Detection of Keratins (K) in Keratinocytes

| Keratinocytes | passage number | K4 | K7 | K8 | K10/1 | K13 | K14 | K17 | K18 | K19 |
|---|---|---|---|---|---|---|---|---|---|---|
| FK0-NR | 2 | ++ | − | ++ | ++ | +++ | ++ | ++ | + | + |
| FK2-NR | 25 | +++ | − | ++ | ++ | +++ | ++ | ++ | + | + |
| DK0-NR | 2 | ++ | − | − | +++ | +++ | +++ | +++ | − | + |
| DK1-NR | 13 | ++ | − | ++ | +++ | +++ | ++ | ++ | + | + |
| DK1-NR | 30 | + | − | ++ | ++ | ++ | ++ | + | ++ | + |
| DK2-NR | 11 | +++ | − | +++ | +++ | +++ | +++ | +++ | +++ | ++ |
| DK3-NR | 36 | + | − | +++ | +++ | +++ | +++ | +++ | +++ | ++ |

Method (Tables 7 and 8): Keratinocytes grown on chamber slides were stained after fixation in pure methanol with antibodies listed in Table 6.
+++: highest concentration of protein, quantified by fluorescence microscope.
−: no protein expression.

6) Expression of Glutathione-S-Transferase: the phase II-enzyme Glutathione-S-transferase (GST) has been analyzed by Northern blot and Western blot technique. All keratinocyte lines express strongly mRNA for GSTπ but not GSTα and GSTμ (Table 9: Method: Northern Blot). The protein-expression profile of GSTα, GSTμ and GSTπ in the cell lines was similar to normal keratinocytes.

TABLE 9

Protein-Expression of GST enzyme

| Keratinocytes | GSTα | GSTμ | GSTπ |
|---|---|---|---|
| FK2-NR | − | − | +++ |
| DK0-NR | − | − | +++ |
| DK1-NR | − | − | +++ |
| DK2-NR | − | − | +++ |
| DK3-NR | − | − | +++ |

7) Essential Fatty Acid (EFA) Metabolism: to analyze and to compare the desaturation and elongation of added EFA in keratinocytes, immortalized (DK1-NR, FK2-NR) and normal keratinocytes were treated with linoleic acid (LA, 15 μM) and α-linolenic acid (LN, 15 μM). For these experiments the EFA-deficient NR-2 (Biofluids Inc.) was used. Cell cultures were treated after reaching confluency and shifting NR-2 high calcium (1.5 mM). Cells were treated 4 days with EFA (renewed after 2 days).
EFA analysis was performed by extraction and separation of phospholipids by TLC (thin layer chromatography) and quantification of fatty acid-methylesters by GLC (gas liquid chromatography). The formation of the desaturation and elongation products of LA (20:4n-6 and 22:4n-6) and LN (20:5n-3, 22:5n-3 and 22:6n-3) could be demonstrated. This metabolic profile was consistent with that observed in normal keratinocytes.

8) Karyotyping: all cell lines were hypodiploid with most chromosome counts in the dipoid range (except DK2-NR with chromosome counts also in the hypotetraploid range). Cells other than those of the analyzed cell lines were not detected in the cultures. This result confirms the purity of the cell lines and the absence of cellular contamination from other sources.

9) In vivo Characterization: the tumorigenicity of immortalized keratinocytes were determined by subcutaneous injection (1-2mio keratinocytes) into nude mice. The tested keratinocyte lines DK2-NR, DK3-NR, FK2-NR are not tumorigenic in nude mice (4 months of incubation). DK3-NR was however weakly tumorigenic in 6 animals among 10 animals after 5 months of incubation.

10) Response to Skin Irritants: the induction of the "stress-gene" TNFα (tumor necrosis factor alpha) after treatment with skin irritants PMA (phorbol-12-myristate-13-acetate), SDS (sodium dodecyl sulfate), DMSO (dimethyl sulfoxide), IL-1 β (interleukin 1 beta), and UV-B (ultraviolet B) was analyzed by Northern blot and biological assays (Table 10). The keratinocyte lines respond to PMA and UV-B and express the protein TNFα even in high passages.
After treatment of immortalized keratinocytes with phorbol esters (PMA) an increase of collagenase (type I) expression was observed.

TABLE 10

Secretion of TNFα in Keratinocytes after Induction with Skin Irritants

Protein activity assay: $^3$H-thymidine incorporation into a TNFα-sensitive cells*.

| Keratinocytes | passage number | TNFα-secretion after induction with | | | | |
|---|---|---|---|---|---|---|
| | | PMA | SDS | DMSO | IL-1β | UV-B |
| DK0-NR | 3 | + | − | − | nt | + |
| DK1-NR | 20–22 | + | + | − | + | + |
| DK1-NR | 32 | + | − | − | nt | + |
| DK2-NR | 16 | + | − | − | − | + |
| DK2-NR | 31 | + | − | − | nt | + | nt: not tested
*sensitive cells: mouse fibrosarcoma cell line WEHI 164 clone 1.14 (ATCC).

11) Organotypic Cultures: the cultivation of human keratinocytes under organotypic conditions (keratinocyte grown air exposed on collagen gel with feeder cells) was also conducted. All keratinocyte lines showed a hyperproliferative morphology compared with normal keratinocytes. These studies have been done in culture medium with serum. The hyperproliferative cell growth was reduced under serum-free conditions (NR-2 with high calcium (1.5 mM) on plastic insert culture dishes without collagen gel and without feeder cells).

EXAMPLE 4

1) Immortalization of melanocytes: a cell suspension produced from skin sample DKO-NR described in example 1, which contains dissociated melanocytes, keratinocytes and fibroblasts, are cultured in the subject NR-3 medium. This is effected by seeding such cells onto culture dishes which are continuously coated with the "cocktail" coating previously described for bronchial cells (Lechner et al., *J. Tiss. Cult. Meth.*, 9:43–48 (1985)). During culturing the primary cell cultures when they reach or substantially reach confluence, the cells are treated for 4 min with trypsin/EDTA (0.025%/0.01%). During this treatment, the melanocytes detached from the keratinocytes culture, and they are collected separately. Primary melanocytes and keratinocytes are thus separated at this stage. The collected primary melanocytes are then seeded in NR-4 serum-free medium which specifically inhibits the growth of keratinocytes. After the primary melanocytes have been cultured and expanded to desired cell numbers in NR-4 serum-free medium using the described coated culture they are then immortalized. Immortalization of keratinocytes is effected with the retroviral construct pLXSHD+SV40(#328) which provides for the expression of the SV40 T-antigen (see Pfeifer et al. Meth. Cell Sci. 17: 83–89, 1995; except virus was collected from packaging cell line forwing in DMEM, 10% fetal calf serum). During infection, the PC-1 serum free medium described in the paper of Pfeifer et al., *Meth. Cell. Sci.*, 14, 83–89 (1995), is used. After immortalization the immortalized cell lines are transferred to the M2 proliferation and differentiation medium (DMEM/F12 medium, Biofluids, No148; can also be bought from M. Olssen, Uppsala, Sweden).

2) Characterization of T-Ag Expressing Human Melanocytes: the expression of melanin-associated proteins of immortalized melanocytes produced according to the invention (especially DM2-NR) was compared to normal melanocytes. It was demonstrated that immortalized cells expressed melanin-associated proteins, melanoma associated antigen (MAA) and HMB45 similar to normal cells, although at lesser levels of expression.

3) Induction of Melanin Synthesis: the melanogenesis of T-Ag expressing melanocyte cell lines (especially line DM2-NR) was compared with normal melanocytes. The melanocytes were treated with the melanogensis inducers tyrosin and theophylline and the melanogenesis inhibitor kojic acid. The melanocyte lines (especially DM2-NR) responded to melanogenesis modulator comparable to normal cells. The induction/inhibition of melanogenesis was also demonstrated to be dose dependent.

EXAMPLE 5 the strain DKO-NR described in example 1 has been immortalized, as described above, with the HPV16 based retrovirus construct pLXSHD+E6/E7 which is depicted in FIG. 2b. Several continuous keratinocytes lines were selected. The analysis results of these lines in terms of differentiation products (cytokeratins, GST, TNFα, Involucrin, Filaggrin, Loricrin, Vimentin) are similar to those obtained for the lines DK2-NR and DK3-NR.

EXAMPLE 6

The composition of the novel NR-3 medium of the invention and several other serum-free medium of the present invention, i.e. NR-1, NR-2 and NR-4, are compared below.

1) Media Composition of NR-1 Medium (see table below)

|  | NR1 [milligram/liter] |
|---|---|
| Amino Acids | |
| L-Alanine | 9.0000 |
| L-arginine, HCl | 316.0000 |
| Asparagine, H$_2$O | 15.0000 |
| L-Aspartic acid | 4.0000 |
| L-Cysteine, HCl, H$_2$O | 42.0000 |
| L-Glutamic acid | 14.8000 |
| Glutamine | 877.0000 |
| Glycine | 7.6000 |
| L-Histidine, HCl, H$_2$O | 50.4000 |
| L-Isoleucine | 98.4000 |
| L-Leucine | 131.2000 |
| L-Lysine, HCl | 36.6000 |
| L-Methionine | 13.4000 |
| L-Phenylalanine | 14.9000 |
| L-Proline | 34.6000 |
| L-Serine | 126.2000 |
| L-Threonine | 23.8000 |
| L-Tryptophan | 9.2000 |
| L-Tyrosine | 13.6000 |
| L-Valine | 70.2000 |
| Inorganic Salts | |
| Ammonium Metavanadate [NH$_4$VO$_3$] | 0.0006 |
| Ammonium Molybdate [(NH$_4$)$_6$Mo$_7$O$_{24}$ × 4H$_2$O] | 0.0010 |
| Calcium Chloride [CaCl$_2$ × 2H$_2$O] | 16.2000 |
| Cupric Sulfate [CuSO$_4$ × 5H$_2$O] | 0.0025 |
| Ferric Sulfate [FeSO$_4$ × 7H$_2$O] | 1.4000 |
| Magnesium Chloride [MgCl$_2$ × 6H$_2$O | 122.0000 |
| Manganese Chloride [MnCl$_2$ × 4H$_2$O] | 0.0002 |
| Nickel Sulfate [NiSO$_4$ × 6H$_2$O] | 0.0003 |
| Potassium Chloride [KCl] | 112.0000 |
| Sodium Acetate | 301.5000 |
| Sodium Bicarbonate [NaHCO$_3$] | 1088.0000 |
| Sodium Chloride [NaCl] | 5200.0000 |
| Sodium Phosphate Dibasic [Na$_2$HPO$_4$ × 7H$_2$O] | 536.0000 |
| Sodium Pyruvate | 55.5000 |
| Sodium Selenite [Na$_2$SeO$_3$] | 0.0050 |
| Sodium Silicate [Na$_2$SiO$_3$ × 9H$_2$O] | 0.1420 |
| Tin Chloride [SnCl$_2$ × 2H$_2$O] | 0.0001 |
| Zinc Sulfate [ZnSO$_4$ × 7H$_2$O] | 0.5100 |
| Vitamins | |
| d-Biotin | 0.0200 |
| d-Calcium Pantothenate | 0.2600 |
| Choline Chloride | 28.0000 |
| Cyanocobalamin (B12) | 0.4100 |
| Folic Acid | 0.7900 |
| i-Inositol | 18.0000 |
| Nicotinamide (B3) | 0.0400 |
| Pyridoxine (B6 × H$_2$O) | 0.0600 |
| Riboflavin (B2) | 0.0400 |
| Others | |
| Adenine | 27.3000 |
| Epidermal growth factor (EGF, human recomb.) | 0.0010 |
| Ethanolamine | 0.0310 |
| Glucose | 1080.0000 |
| HEPES | 6000.0000 |
| Hydrocortisone | 0.5000 |
| Insulin (bovine) | 5.0000 |
| Phenol Red | 1.2000 |
| Phosphoethanolamine | 0.0710 |
| Putrescine 2HCl | 0.1600 |
| Thiamine HCl | 0.3400 |
| Thioctic Acid | 0.2100 |
| Thymidine | 0.7300 |
| Transferrin (human) | 10.0000 |
| Osmolarity | 280-285 mOsm/kg |

2) Media Composition of NR-2 Medium: same as NR-1 but supplemented with bovine pituitary extract (Biofluid Inc.) at 35 mg/l, and containing antibiotics (Gibco BRL, Life Technologies Inc.) fungizone (0.25 mg/l) penicillin (10.000 units/l) and streptomycin (10 mg/l).

3) Media Composition of NR-3: same substituents as NR-2 but supplemented with epinephrine (Biofluid Inc.) 250 µg/l.

4) Media Composition of NR-4: same substituents as NR-2 but supplemented with βFGF (3 μg/l) (basic fibroblast growth factor obtained from Sigma Inc.) and phorbol 12-myristate-13-acetate (10 μg/l) (PMA) (C.C.R. Inc.).

Although the invention has been described in considerable detail with regard to certain preferred embodiments thereof, other embodiments within the scope of the teachings of the present invention are possible. Accordingly, neither the disclosure nor the claims which follow, are intended, nor should be construed to be, limited by the description of the preferred embodiments contained herein.

What is claimed is:

1. A retroviral-infected immortalized human keratinocyte or melanocyte cell line prepared by infection of human keratinocytes or melanocytes with a retroviral construct under conditions such that immortalizes cells, which immortalized human keratinocyte or melanocyte cell line retains the ability to differentiate and to express proteins and enzymes which are expressed by normal differentiated keratinocytes or melanocytes even after at least 20 passages in tissue culture, wherein the keratinocyte cell line expresses keratin proteins expressed by normal differentiated keratinocytes and the melanocyte cell line expresses melanin proteins expressed by normal differentiated melanocytes.

2. The retroviral-infected immortalized keratinocyte cell line according to claim 1, wherein said cell line expresses other proteins which are expressed by normal differentiated keratinocytes.

3. The retroviral-infected immortalized keratinocyte cell line according to claim 2, wherein said keratin proteins include Keratin K1/10, Keratin K14 and said other proteins include involucrin, filaggrin and loricrin.

4. The retroviral-infected immortalized keratinocyte cell line according to claim 1, wherein the cell line exhibits a CYP450 profile which is identical or substantially identical to that of normal differentiated keratinocytes.

5. The retroviral-infected An immortalized keratinocyte cell line according to claim 4, wherein the cell line expresses CYP450 1A1, 2C, 2E1 and 3A5 but does not express CYP450 1A2, 2A6, 2B6 and 2D6.

6. The retroviral-infected immortalized human keratinocyte cell line according to claim 1, which is produced under serum-free conditions without the use of feeder cells.

7. The retroviral-infected immortalized human melanocyte cell line according to claim 1, which is produced under serum-free conditions without the use of feeder cells.

8. An SV40 T-Antigen immortalized human skin cell line selected from the group consisting of the keratinocyte lines DK2-NR (DSM ACC2238), DK3-NR (DSM ACC2239) and FK2-NR (DSM ACC2240) and the melanocyte line DM2-NR (CNCM I-1796).

9. The retroviral-infected immortalized keratinocyte or melanocyte cell line according to claim 1, which expresses mRNA encoding glutathione-S-transferase GST-$\pi$, GST-$\mu$, and GST-$\alpha$.

10. The retroviral-infected immortalized keratinocyte cell line according to claim 1, which when cultured in organotypic culture forms a highly stratified and polarized epithelium having cornified superficial layers in the absence of serum or feeder cells.

11. The retroviral-infected immortalized keratinocyte cell line according to claim 1, which expresses collagenase type 1 and TNF-$\alpha$ when treated with phorbol esters.

12. A retroviral-infected immortalized human keratinocyte or melanocyte cell line that retains the ability to differentiate and to express proteins and enzymes which are expressed by normal differentiated keratinocytes or melanocytes even after at least 20 passages in tissue culture, wherein the cell line is prepared by:

(i) obtaining a human skin tissue sample;

(ii) preparing said skin sample for culturing in vitro;

(iii) obtaining keratinocytes and/or melanocytes from said prepared skin sample and seeding said keratinocytes and/or melanocytes into a serum-free growth medium, onto culture plates provided with a coating comprising fibronectin, type 1 collagen and BSA which facilitates cell attachment and growth;

(iv) changing the medium as necessary to optimize confluent growth of the cultured cells while continuously maintaining the coating on the culture plates;

(v) transferring the keratinocytes or melanocytes into a serum-free selection medium onto similarly precoated culture plates;

(vi) infecting the keratinocytes or melanocytes with a retroviral construct that immortalizes cells;

(vii) transferring the resultant immortalized keratinocytes or melanocytes to a serum-free proliferation medium suitable for proliferating immortalized keratinocytes or melanocytes onto similarly precoated culture plates; and (viii) transferring the resultant proliferated keratinocytes to a serum-free differentiation medium which contains high calcium onto similarly precoated culture dishes.

13. The cell line according to claim 12 further comprising at least one of the following:

the retroviral construct is the SV40 construct pLXSHD+SV40(#328) or the HPV16 construct pLXSHD+E6/E7;

the serum-free medium in step (iii) is NR-3 medium;

the medium in step (v) is the NR-3 medium or the NR-4 medium;

the proliferation medium in step (vii) is the NR-2 medium or the NR-3 medium and M2 medium for melanocytes; and the differentiation medium in step (viii) is the NR-2 medium or modified MCDB 153 medium which contains a calcium content of at least 1.5 mM.

14. The retroviral-infected immortalized human melanocyte cell line according to claim 1, wherein the cell line expresses vimentin, which is expressed by normal differentiated melanocyte cell line.

15. The retroviral-infected immortalized human keratinocyte or melanocyte cell line according to claim 1, where the cell line retains the ability to differentiate and to express proteins and enzymes expressed by normal differentiated keratinocytes or melanocytes even after at least 30 passages.

16. The retroviral-infected immortalized human keratinocyte or melanocyte cell line according to claim 1, where the cell line retains the ability to differentiate and to express proteins and enzymes expressed by normal differentiated keratinocytes or melanocytes even after at least 50 passages.

* * * * *